(12) United States Patent
Reategui et al.

(10) Patent No.: US 10,551,376 B2
(45) Date of Patent: Feb. 4, 2020

(54) CAPTURE AND RELEASE OF PARTICLES FROM LIQUID SAMPLES

(71) Applicant: The General Hospital Corporation, Boston, MA (US)

(72) Inventors: Eduardo Reategui, Revere, MA (US); Shannon Stott, Stoneham, MA (US); Mehmet Toner, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 317 days.

(21) Appl. No.: 14/764,855

(22) PCT Filed: Feb. 3, 2014

(86) PCT No.: PCT/US2014/014463
§ 371 (c)(1),
(2) Date: Jul. 30, 2015

(87) PCT Pub. No.: WO2014/121204
PCT Pub. Date: Aug. 7, 2014

(65) Prior Publication Data
US 2015/0369804 A1 Dec. 24, 2015

Related U.S. Application Data

(60) Provisional application No. 61/759,684, filed on Feb. 1, 2013.

(51) Int. Cl.
| | | |
|---|---|---|
| *G01N 33/53* | (2006.01) | |
| *G01N 33/543* | (2006.01) | |
| *G01N 33/574* | (2006.01) | |

(52) U.S. Cl.
CPC . *G01N 33/54393* (2013.01); *G01N 33/57492* (2013.01); *G01N 2333/71* (2013.01); *G01N 2400/00* (2013.01)

(58) Field of Classification Search
CPC ....... G01N 33/54393; G01N 33/57492; G01N 2400/00; G01N 2333/71; G01N 33/56966; G01N 33/54366; G01N 33/544; G01N 33/53
See application file for complete search history.

(56) References Cited

U.S. PATENT DOCUMENTS

| | | |
|---|---|---|
| 5,073,341 A | 12/1991 | Hargreaves |
| 5,637,469 A | 6/1997 | Wilding et al. |
| 2005/0244843 A1 | 11/2005 | Chen et al. |
| 2007/0134713 A1 | 6/2007 | Cao |
| 2009/0298067 A1 | 12/2009 | Irimia et al. |
| 2011/0086771 A1 | 4/2011 | Mahant et al. |
| 2012/0003711 A1 | 1/2012 | Tseng et al. |
| 2012/0270209 A1 | 10/2012 | Shah et al. |

FOREIGN PATENT DOCUMENTS

| | | |
|---|---|---|
| WO | 2010/129283 | 11/2010 |
| WO | 2012/106384 | 8/2012 |
| WO | 2012/106658 | 8/2012 |

OTHER PUBLICATIONS

Nishida et al (2002, Polymer Journal, vol. 34, No. 3, pp. 166-174).*
Adams et al. "Highly efficient circulating tumor cell isolating from whole blood and label free enumeration using polymer-based microfluidics with an integrated conductivity sensor," J Am Chem Soc., Aug. 2008, 130: 8633-8641.
Cheng et al., "A microfluidic device for practical label-free CD4+ T cell counting of HIV-infected subjects," Lab on a Chip, 2007, 7:170-178.
European Office Action in European Application No. 14745825.1, dated Aug. 17, 2016, 5 pages.
International Preliminary Report on Patentability in International Application No. PCT/US2014/014463, dated Aug. 4, 2015, 8 pages.
International Search Report in International Application No. PCT/US2010/032585, dated Dec. 29, 2010, 5 pages.
Nagrath et al., "Isolation of rare circulating tumour cells frl cancer patients by microchip technology," Nature, Dec. 2007, 450(7173): 1235-1239.
Reategui et al., "Tunable Nanostructured Coating for the Capture and Selective Release of Viable Circulating Tumor Cells", Advanced Materials, Jan. 2015, 27(9): 1593-1599.
Shah et al., "Biopolymer System for Cell Recovery from Microfluidic Cell Capture Devices", Analytical Chemistry, Mar. 2012, 84(8): 3682-3688.
Sheng et al., "Capture, release and culture of circulating tumor cells from pancreatic cancer patients using an enhanced mixing chip," Lab on a Chip, 2014, 14(29): 89-98.
Supplementary European Search Report in European Application No. 14745825.1, dated Apr. 8, 2016, 6 pages.
International Search Report and Written Opinion dated Apr. 16, 2014 in international application No. PCT/US2014/014463, 15 pgs.
Hou et al. Capture and stimulated release of circulating tumor cells on polymer-grafted silicon nanostructures. Advanced Materials, 25(11): 1547-1551 (Mar. 2013).

\* cited by examiner

*Primary Examiner* — Julie Wu
*Assistant Examiner* — Carmencita M Belei
(74) *Attorney, Agent, or Firm* — Fish & Richardson P.C.

(57) ABSTRACT

Systems, methods, and devices for selective capture and release of target particles, e.g., living cells, from liquid samples, e.g., blood, are provided. The particle capture systems include a substrate; a first layer of gelatin bound to the substrate by physical adsorption, wherein the gelatin is functionalized with a plurality of first members of a binding pair; a second layer of gelatin wherein the gelatin is functionalized with a plurality of the first members of the binding pair and the second layer is bound to the first layer via a plurality of second members of the binding pair that are associated with the first members of the binding pair on both the first and the second layers; and a plurality of nanostructures bound to the second members of the binding pair and to one or more particle-binding moieties that selectively bind to the target particles.

13 Claims, 7 Drawing Sheets

CAPTURE AND RELEASE OF PARTICLES FROM LIQUID SAMPLES

CROSS-REFERENCE TO RELATED APPLICATIONS

This application is a U.S. National Phase Application under 35 U.S.C. § 371 of International Patent Application No. PCT/US2014/014463, filed on Feb. 3, 2014, which claims the benefit of U.S. Provisional Patent Application Ser. No. 61/759,684, filed on Feb. 1, 2013, the entire contents of which are incorporated herein by reference.

FIELD OF THE INVENTION

This disclosure relates to systems, devices, and methods for selectively binding and releasing particles, e.g., living cells, from liquid samples, e.g., blood.

BACKGROUND

Isolation of specific target particle populations, e.g., living cells or microvesicles, from complex mixtures such as whole blood has significant utility in both clinical practice and basic medical research. A variety of approaches may be used to separate particles from a heterogeneous sample. For example, some techniques can use functionalized materials to capture cells based on cell surface markers that are particular to the target cell population using specific capture moieties present on or in the functionalized materials. Such capture moieties can include antibodies or other specific binding molecules, such as aptamers or selectins. For example, a microfluidic affinity-based chip that is configured to isolate rare circulating tumor cells (CTCs) from whole blood of cancer patients is described, e.g., in Nagrath et al., "Isolation of rare circulating tumour cells in cancer patients by microchip technology," Nature 450 (2007), pp. 1235-1239, or Stott et. al., "Isolation of circulating tumor cells using microvortex-generating herringbone-chip," PNAS 107 (2010), pp. 18392-18397. These CTCs may disseminate from the tumor and are observed to be present in numbers that tend to correlate with patients' clinical courses. These CTCs may also be involved in metastasis. Accordingly, such microfluidic chip technology may be used in diagnostic and prognostic devices for oncological applications. At present, limited phenotyping and genotyping of these rare cells can be achieved because the CTCs tend to remain attached to the substrate (e.g., a silicon-based chip).

SUMMARY

The present disclosure provides systems, methods, and devices for the selective capture and release of target particles, e.g., living cells, microvesicles, or exosomes, from liquid samples, e.g., blood or serum. The present disclosure is based, at least in part, on the development of new particle capture systems that include a substrate; a first layer of gelatin bound to the substrate by physical adsorption, wherein the gelatin is functionalized with a plurality of first members of a binding pair; a second layer of gelatin wherein the gelatin is functionalized with a plurality of the first members of the binding pair and the second layer is bound to the first layer via a plurality of second members of the binding pair that are associated with the first members of the binding pair on both the first and the second layers. Optionally, the systems can further include one or more subsequent layers of gelatin, each bound to a previous layer by second members of the binding pair. All systems further include a plurality of nanostructures, wherein the nanostructures are bound to the second members of the binding pair and to one or more particle-binding moieties that selectively bind to the target particles, wherein the nanostructures are bound to a top layer of gelatin by the second members of the binding pair.

The target particles can be selectively captured from a liquid sample by contacting the liquid sample to the particle capture systems to enable the one or more particle-binding moieties to bind to target particles in the sample. The captured particles can then be bulk released from the systems by melting the gelatin layers at an increased temperature, e.g., a temperature over 30° C., e.g., 37° C. The captured particles can also be selectively released from the systems by increasing a localized shear stress on the gelatin layers, e.g., by applying a frequency-controlled force with a microtip.

In one aspect, the present disclosure features systems for selectively capturing and releasing one or more target particles from a liquid sample. These particle capture systems include a substrate, e.g., a flat slide, a channel in a microfluidic device, or a microbead, which is bound with a first layer of gelatin that is functionalized with a first member of a binding pair, e.g., biotin. The first layer of gelatin is bound to the substrate by physical adsorption. These particle capture systems further include a second layer of gelatin that is also functionalized with a plurality of the first members of the binding pair and is bound to the first layer via a plurality of second members of the binding pair, e.g., avidin, streptavidin, or neutravidin to bind to biotin. The second members of the binding pair are associated with the first members of the binding pair on both the first and the second layers. Optionally one or more subsequent layers of functionalized gelatin can be included, wherein each new layer is bound to a previous layer by the second members of the binding pair. These particle capture systems also include a plurality of nanostructures, e.g., nanoparticles, nanospheres, nanotubes, or nanorods, which are bound to the surface of the top gelatin layer by the second members of the binding pair. Each of the nanostructures is bound to the second members of the binding pair and to one or more particle-binding moieties that selectively bind to the target particles.

In another aspect, the present disclosure features methods of selectively capturing and releasing one or more target particles from a liquid sample using the particle capture systems described herein. These methods include contacting the liquid sample to the particle capture systems to enable the one or more particle-binding moieties on the nanostructures to bind to target particles in the sample. In some embodiments, these methods further include releasing the bound target particles from the system by melting the gelatin layers at an increased temperature, e.g., at a temperature over 30° C., e.g., 37° C. In some embodiments, these methods further include selectively releasing the bound target particles from the system by applying a localized shear stress to one or more of the gelatin layers, e.g., by applying a frequency-controlled force with a microtip to at least a top gelatin layer.

In some embodiments, the target particles are living cells or microvesicles, e.g., leucocytes, CD4+ T-cells, fetal cells in maternal blood, or circulating tumor cells (CTC). The particle-binding moieties can include antibodies that specifically bind living cells or microvesicles. For example, when the target particles are CTCs, the antibodies can be, for example, any one or more of anti-EpCAM, anti-HER2, and anti-EGFR antibodies. For white blood cells, the antibodies can include, e.g., any one or more of anti-CD45, anti-CD16, and anti-CD14 antibodies. For fetal nucleated red blood cells in maternal blood, the antibodies can include, for example, any one or more of anti-fetal hemoglobin and anti-embryonic hemoglobin antibodies. For microvesicles, the antibodies include any one or more of anti-CD9, anti-CD63, anti-CD81, and anti-CD31.

In another aspect, the present disclosure features methods of making a target particle capturing system. The methods include (a) obtaining a substrate, e.g., a flat slide, a channel in a microfluidic device, or a microbead; (b) forming a first layer of gelatin on the substrate by physical adsorption, wherein the gelatin is functionalized with a plurality of first members of a binding pair, e.g., biotin; (c) contacting the first layer of gelatin with second members of the binding pair, e.g., avidin, streptavidin, or neutravidin; (d) forming a second layer of gelatin that is functionalized with a plurality of the first members of the binding pair and the second layer is bound to the first layer via a plurality of second members of the binding pair that are associated with the first members of the binding pair on both the first and the second layers; (d) optionally forming one or more subsequent layers of gelatin, each bound to a previous layer by second members of the binding pair; and (e) contacting the last formed gelatin layer with a solution including nanostructures, which are bound to second members of the binding pair and to one or more particle-binding moieties that selectively bind to the target particles.

In a further aspect, the present disclosure features devices for selectively releasing one or more particles from a gel. These devices can include a microtip and a vibrator that is connected to the microtip and moves the microtip at a controlled frequency. When contacting with the gel, the microtip can produce a localized shear stress in the gel at the controlled frequency, and thereby induces the release of one or a few selected particles from the gel. In some implementations, the vibrator includes one or more magnets and an electromagnet. In some implementations, the vibrator includes a piezoelectric element.

As used herein, "functionalizing" a material or a "functionalized" material refers to a chemical modification of the material to modify the reactivity of the material. Similarly, functionalizing a surface or a functionalized surface refers to the chemical modification of the surface to modify the reactivity of the surface. For example, the material can be chemically modified by oxidizing, reducing, aminating, or carboxylating one or more chemical functional groups. Functionalizing the surface can include, for example, contacting the surface (e.g., glass) with a chemical compound that introduces amine moieties to the surface. Functionalizing can be performed in one or more chemical reaction steps. A material can be functionalized by reactive contact with one or more functionalizing agents, which can be one or more chemical compounds that react with at least a portion of the hydrogel. For example, biotin-NHS can be bound to primary amines on a gelatin.

As used herein, a "substrate" is any material that has a surface to which functionalized gelatin layers can be applied as described herein. For example, a substrate can be a material with a relatively flat or curved surface such as a plastic or glass microscope slide. In other implementations, the substrate can be a device with a complex, three-dimensional surface, such as the one or more channels in a microfluidic device, or the substrate can be a bead or particle or a collection of a plurality of beads or other particles of various sizes, e.g., microbeads or microparticles, and materials, e.g., glass, ceramic, metal, or plastic, to the surface of which the functionalized gelatin can be applied.

The new systems and methods provide several advantages. For example, the systems provide a low cost, unique tunable capacity for the isolation as well as the release of rare particles, such as target circulating tumor cells ("CTCs"), microvesicles, exosomes, fungal cells, and fetal cells in maternal blood, at the single cell level. These extremely rare cells can be captured with high yield and accuracy, and then released either in bulk or one or a few cells at a time. The ability to release a few cells at a time is a major advantage for downstream molecular assays, because it provides highly pure samples. In addition, the release efficiency and viability of the captured and released cells is very high. The different release methods enable multiple type of assays within the same sample (e.g., staining for immunofluorescence, cell culture, molecular analysis). The non-fouling, physiologically friendly methods to release the cells (by raising the temperature, e.g., to body temperature) also help to maintain cell integrity for downstream cell culture and/or RNA/DNA analysis. Moreover, the extremely thin (nanometer-scale) coatings applied by the new methods enable one to coat complex 3D geometries of microfluidic devices such as herringbone structures, e.g., as described and illustrated in Toner et al., US Published Patent Application No. US2011/0294187, and other microfluidic devices, e.g., as described in Toner et al., U.S. Pat. No. 8,304,230, and Toner et al., U.S. Pat. No. 8,186,913, the contents of which are incorporated herein by reference in their entireties.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. All publications, patent applications, patents, and other references mentioned herein are incorporated by reference in their entirety. In case of conflicting subject matter, the present specification, including definitions, will control. In addition, the materials, methods, and examples are illustrative only and not intended to be limiting.

These and other objects, features and advantages of the present invention will become apparent upon reading the following detailed description of embodiments of the invention, when taken in conjunction with the appended claims. The details of one or more embodiments of the invention are set forth in the accompanying drawings and the description below.

DETAILED DESCRIPTION

The present disclosure provides systems, methods, and devices for selective capture and release of target particles of different sizes, e.g., living cells or microvesicles, for example rare cells, from liquid samples, e.g., blood or serum. In general, the new particle capture systems include a substrate, e.g., a 3D substrate, such as one or more channels within a microfluidic device, a microbead or other spherical or particulate substrate, or a flat substrate, such as a microscope slide, which is coated with a first layer of gelatin that is functionalized with a first member of a binding pair, e.g., biotin. The first layer of gelatin is bound to the substrate by physical adsorption. A second layer of gelatin also functionalized with a plurality of the first members of the binding pair is bound to the first layer via a plurality of second members of the binding pair, e.g., avidin or streptavidin to bind to biotin, that are associated with the first members of the binding pair on both the first and the second layers. Optionally one or more subsequent layers of functionalized gelatin can be included, wherein each new layer is bound to a previous layer by second members of the binding pair.

As noted, the presently disclosed methods of making the particle capture systems use protein physisorption physics (e.g., hydrogen bonding, electrostatic interactions, hydrophobic interactions) to deposit a first gelatin layer on a substrate, thus nanometer-size thicknesses can be achieved. In addition, the new methods enable the coating of complex 3D geometries in microfluidic devices such as herringbone structures. Furthermore, gelatin exhibits an amphoteric behavior (positive and negative charges are present in the polymer at certain values of pH), and therefore self-assembly of gelatin in multiple layers is possible. This is different from forming polymeric layers using standard layer-by-layer methodologies that require the use of two oppositely charged polymers. In addition, when the gelatin is functionalized as described herein, the gelatin is provided with increased thermal stability.

Once the layers are completed a plurality of nanostructures, e.g., nanoparticles, nanospheres, nanotubes, or nanorods, are bound to the surface of the top gelatin layer. Each of the nanostructures is bound to the second members of the binding pair and to one or more particle-binding moieties that selectively bind to the target particles. The nanostructures are bound to the top layer of gelatin by the second members of the binding pair. The nanostructures add surface roughness to the top gelatin layer and create two additional benefits; (i) higher local concentration of the particle-binding moieties per unit area, and (ii) multiple orientations of the particle-binding moieties around the surface of the nanostructures which can provide high particle capture efficiency.

Target particles can be selectively captured from a liquid sample by contacting the liquid sample to the bioresponsive-nanostructured particle capture systems disclosed herein to enable the one or more particle-binding moieties to bind to target particles in the sample. The target particles can then be released from the substrate, e.g., a slide or a channel within a microfluidic device, via either of two release mechanisms. First, by increasing temperature, e.g., over 30° C., e.g., 37° C., capture particles can be released in a bulk fashion. Second, by increasing a localized shear stress in the gelatin, e.g., by applying a frequency-controlled force with a vibrating device, e.g., the microtip devices described herein, single cells can be selectively released from the substrate. The versatility of the particle capture systems allows a practitioner to perform various assays with low or high complexity. For low complexity assays such as cell enumeration, culturing and staining, bulk release is sufficient. For high complexity assays such as single cell genomics, the selective release may be preferred.

Methods of Making Particle Capture Systems

The particle capture systems disclosed herein can be formed by using a modified layer-by-layer (LBL) process. Such LBL process can start with obtaining a substrate, e.g., glass or PDMS. The substrate can be a microscope slide or one or more channels, e.g., within a microfluidic device. The substrate can then be exposed to a gelatin solution comprising gelatin functionalized with a plurality of the first members of a binding pair, e.g., biotinylated gelatin, at a concentration and for a period of time sufficient for the gelatin to bind to the substrate, e.g., 5, 10, 15, or 20 minutes, thereby forming a first layer of gelatin on the substrate by physical adsorption. The time of exposure is one factor in selecting the thickness of the coating, with the maximum thickness being attained at about 15 minutes. Longer times will not add much to the thickness and shorter times will result in a thinner coating. The exposure can be accomplished by flowing the gelatin solution over or onto the substrate and is done at room temperature. The idea is for the gelatin to physically adsorb to the substrate without gelling.

The excess gelatin solution can be washed out with a buffer, e.g., phosphate-buffer saline (PBS). This physisorbed gelatin layer interacts strongly with the substrate, e.g., PDMS or glass surface, and is not sensitive to temperature changes up to 37° C. The thickness of the physisorbed layer also depends on the initial concentration of the functionalized gelatin solution, which can be about 0.1% to about 2.5%, e.g., about 0.5% to about 2%, about 0.5% to about 1.5%, about 0.6% to about 1.4%, about 0.7% to about 1.3%, about 0.8% to about 1.2%, about 0.9% to about 1.1%. All concentrations are weight/volume. FIG. 1C shows the thickness of one or multiple gelatin layers in an exemplary particle capture system. The dotted-line represents the initial physisorbed, e.g., physically adsorbed, gelatin layer.

Next, the first layer of gelatin can be contacted with a solution comprising the second members of the binding pair, e.g., avidin, neutravidin, or streptavidin, for a period of time sufficient to enable the members of the binding pair to bind each other, e.g., 15 minutes. A second layer of gelatin can be formed by exposing the deposited layers to the functionalized gelatin solution again for a period of time sufficient to enable the first members of the binding pair on the gelatin in solution to bind the second members of the binding pair on the deposited layers, e.g., 15 minutes.

Thus, the second layer is bound to the first layer via a plurality of the second members of the binding pair that are associated with the first members of the binding pair on both the first and the second layers. The deposited second layer of gelatin can then be contacted with a solution comprising the second members of the binding pair again to allow the members of the binding pair to bind to each other. These steps can be repeated to form one or more subsequent layers of gelatin, each bound to a previous layer by the second members of the binding pair. The second and subsequent gelatin layers are temperature-responsive layers. The gelatin layers are formed at a temperature of about 10° C. to about 23° C.

Finally, the solidified gelatin layers can be contacted with a solution comprising nanostructures that are bound to the second members of the binding pair and to one or more particle-binding moieties that can selectively bind the target particles for a period of time sufficient for the nanostructures to bind to the functional groups on the gelatin layers, e.g., 30 minutes. The nanostructures are about 50 to 250 nm, e.g., 75 to 150 nm, e.g., 100 nm, in size and can be, for example, nanoparticles, nanotubes, nanorods, or nanospheres.

Figure 1A:
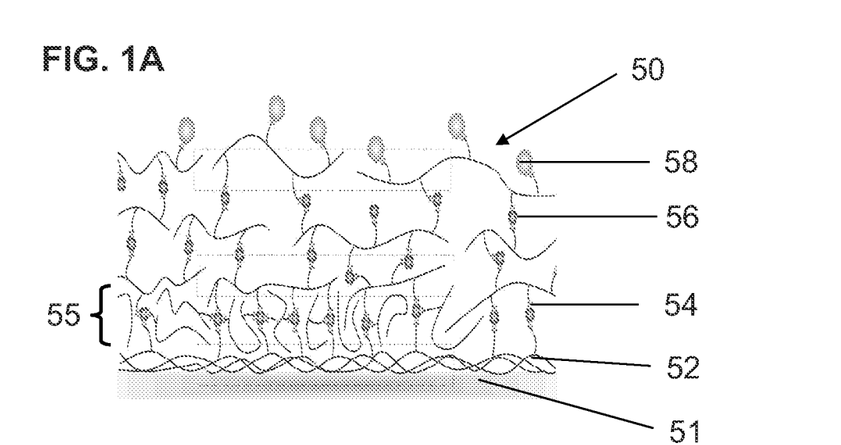
FIG. 1A is a schematic, highly magnified illustration of one implementation of a particle capture system on a substrate, such as a microscope slide, microfluidic channel, or microbead surface.

By using the LBL process described above, systems for selectively capturing and releasing one or more target particles from a liquid sample as illustrated in FIG. 1A can be formed. FIG. 1A illustrates one example of a particle capture and release system 50, which includes a substrate 51 (e.g., a glass slide, microbead surface, or channel of a microfluidic device); a first layer of gelatin 52 bound to the substrate 50 by physical adsorption, wherein the gelatin is functionalized with a plurality of first members of a binding pair 54; a second layer of gelatin 55 wherein the gelatin is functionalized with a plurality of the first members of the binding pair 54 and the second layer is bound to the first layer 52 via a plurality of second members of the binding pair 56 that are associated with the first members of the binding pair on both the first and the second layers; optionally one or more subsequent layers of gelatin, each bound to a previous layer by second members of the binding pair, and a plurality of nanostructures 58 that are bound to second members of the binding pair 56 and to one or more particle-binding moieties that selectively bind to the target particles, wherein the nanostructures are bound to a top layer of gelatin by the second members of the binding pair 56.

Figure 1B:
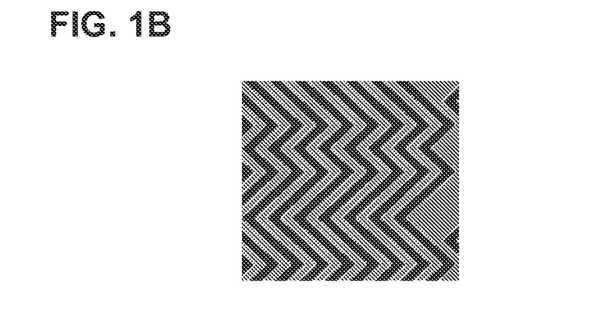
FIG. 1B is a representation of a microfluidic device with a so-called "herringbone" pattern of channels.
Figure 1C:
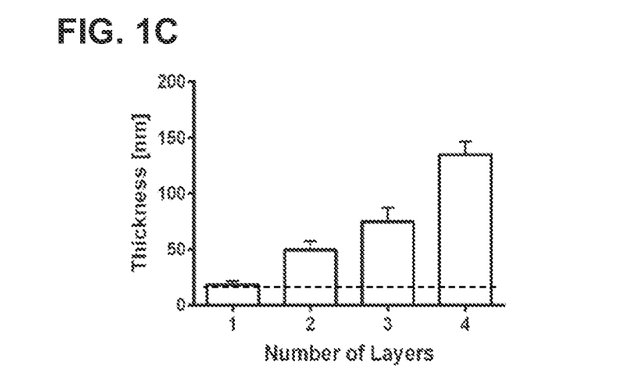
FIG. 1C is a bar graph showing the thickness of one or multiple gelatin layers. The dotted-line represents the initial physisorbed, e.g., physically adsorbed, gelatin layer. The resulting thickness per layer is dependent on the original concentration of gelatin.

FIG. 1B is a representation of a microfluidic device with a so-called "herringbone" pattern of channels. The gelatin layers are formed on the surfaces of the channels, e.g., the bottom and/or side walls, within the microfluidic device.

The binding pairs used in the particle capture systems can be those commonly known in the art, e.g., biotin/streptavidin, biotin/neutravidin, nucleic acid/complementary nucleic acid, substrate/binding protein, antigen/antibody, hormone/receptor, enzyme/substrate, opposite charged polyelectrolytes polymers, and the like. The antibodies can include, for example, anti-EpCAM, anti-HER2, and anti-EGFR antibodies.

In some implementations, the substrate comprises a silica-containing material (e.g., glass, PDMS, sol-gel product or reactant). In some implementations, the substrate can be a polymeric thermoplastic material, e.g., commodity or engineered polyolefin polymers or copolymers including but not limited to polyacrylics (Lucite®, polymethylmethacrylate); polycarbonate (Lexan®, Calibre®, etc.); polyvinyl chloride, polyethylene, polypropylene, polyethylene terephthalate, cycloolefins (cycloolefin copolymer (COC, or TOPAS), or cycloolefin polymer (COP or Zeonor®); polystyrene; epoxies, etc. In some embodiments, the substrate could be a thermosetting plastic, such as epoxies (mixture of epoxide resin with polyamine resin), including fiber-reinforced plastic materials. In some implementations, the substrate could be any of these polymeric materials functionalized with silica. In general, for polymeric substrates, the Young's modulus can be within a range of about 0.2 to 4.0 GPa, e.g., 250 to 2000 KPa, or 360 to 870 KPa, so that the substrate can easily be used for selective release with an applied shear stress as described herein.

In other implementations, the substrate can be metallic (gold, silver, platinum, copper, or aluminum), metal oxides (copper oxide, aluminum oxide, silver oxide, indium tin oxide, etc.); inorganic materials including semiconductor materials and magnetic materials. In some implementations, the substrate can be a combination of silica, polymeric, metallic, or inorganic materials listed above.

Capturing and Releasing Target Particles Using Particle Capture Systems

The particle capture systems described herein can be used to selectively capture target particles from a liquid sample. For example, a liquid sample can be applied to the particle capture systems for a period of time sufficient to enable the particle-binding moieties on the nanostructures to bind target particles in the liquid sample. For example, the liquid sample can be flowed onto or into the substrate, or the substrate can be dipped into the liquid sample.

The captured particles can be released from the particle capture systems by two ways: bulk release or selective release. Bulk release occurs when the bound target particles are released from the capture systems by melting the external gelatin layers at an increased temperature. For bulk release to occur, the particle capture systems must include the second and a few subsequent gelatin layers, for example, three, four, five, or more gelatin layers in total. When the temperature is below 30° C., e.g., at room temperature, the gelatin layers stay deposited and the release of captured particles is negligible. An increase in the temperature to over 30° C., e.g., to 37° C., leads to melting and detachment of the external gelatin layers from the substrate.

Selective release occurs when a localized shear stress is generated in the gelatin layer, e.g., by applying a frequency-controlled force with a vibrating device, e.g., a microtip device described herein, to the gelatin layers. The microtip device can produce a controlled vibration at the surface of the gelatin such that the gelatin is locally removed by shear stress. The size of the gelatin removed depends on the frequency of vibration and a release radius is defined.

Figure 4A:
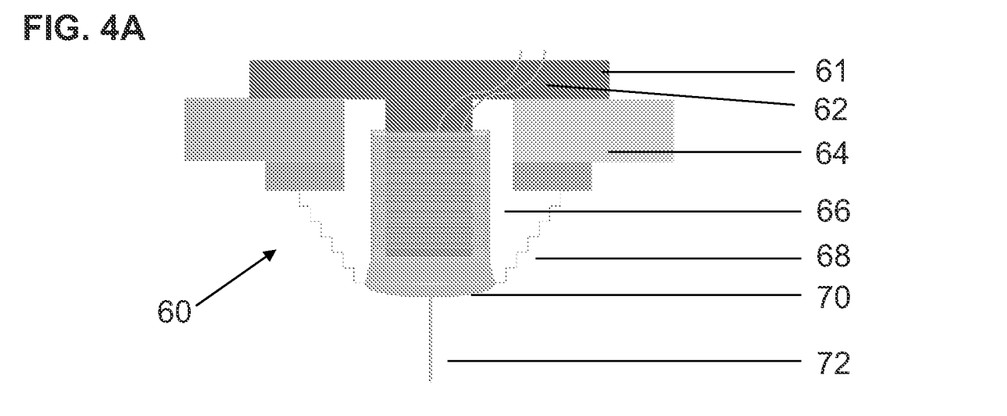
FIG. 4A is a schematic illustration of one implementation of a device for selectively releasing one or more captured particles in a gel.

One way to achieve selective release of captured particles is by using a microtip device 60 as illustrated in FIG. 4A. Such a device 60 for selectively releasing one or more captured particles in a gel, comprises (1) a microtip 72; and (2) a vibrator mechanism that is connected to the microtip and moves the microtip at a controlled frequency, wherein the microtip when contacting the gel produces a localized shear stress in the gel at the controlled frequency, and releases one or more captured particles from the gel. The vibrator mechanism can consist of copper coil and cone 66 mounted on a support 61, and magnets 64. The copper coil and cone 66 are connected with an electricity source through connector 62.

The microtip device 60 can further include a film 70, which wraps around the copper coil and cone 66. One end of the microtip 72 itself is mounted, e.g., perpendicularly, on the copper coil and cone 66 to ensure movement only in the z-direction (to bring it into contact with the gel). The microtip can have a diameter of 50-150 µm, e.g., 80 µm. The device 60 can further include one or more holders 68 that provide support to the film 70, e.g., by connecting the film 70 with another components of the device 60, e.g., the support 61 or the magnets 64. In operation, the vibrator mechanism generates vibration at a controlled frequency when electric current passes through the copper coil 66. The vibration moves the microtip 72 at the controlled frequency. When the microtip 72 contacts the gelatin layers of the particle capture systems, it creates a localized shear stress in the gelatin layer and releases one or more captured particles from the system. The size of release radius is based on the magnitude of the localized shear stress, which can be controlled by the frequency of vibration. In the past it has been shown the possibility of using shear stress as a mechanism of particle release, one example is the device presented in Sheng et. al., Lab on a Chip, 14 (29), 2014, p 89-98. However, flow rates presented in this device are excessively high (~18 mL/h) and the amount of shear stress may damage potential target cells and it does not offer release selectivity at all since the shear stress is uniformly applied to the entire device.

In some embodiments, the target particles are living cells or microvesicles, e.g., leucocytes, CD4+ T-cells, fetal cells in maternal blood, or circulating tumor cells (CTC). The particle-binding moieties can include antibodies that specifically bind living cells or microvesicles. For example, when the target particles are CTCs, the antibodies can be, for example, any one or more of anti-EpCAM, anti-HER2, and anti-EGFR antibodies. For white blood cells, the antibodies can include, e.g., any one or more of anti-CD45, anti-CD16, and anti-CD14 antibodies. For fetal nucleated red blood cells in maternal blood, the antibodies can include, for example, any one or more of anti-fetal hemoglobin and anti-embryonic hemoglobin antibodies. For microvesicles, the antibodies include any one or more of anti-CD9, anti-CD63, anti-CD81, and anti-CD31.

The particle capture systems described herein can be included in microfluidic devices to capture and then release living cells from a biological sample, e.g., blood. Examples of elastomer microchannels are described, e.g., in Cheng et al., "A microfluidic device for practical label-free CD4+ T cell counting of HIV-infected subjects." Lab on a Chip 7 (2007), pp. 170-178. Preparation of microchannels with functionalized gels are described, e.g., in Nagrath et al., "Isolation of rare circulating tumour cells in cancer patients by microchip technology," Nature 450 (2007), pp. 1235-1239, both of which are incorporated herein by reference in their entireties.

Further features and aspects of the present invention are described in the following non-limiting examples.

EXAMPLES

Example 1: Synthesis and Characterization of One Example of a Particle Capture System: Gel-Chip Single and 8-channel herringbone microfluidic devices were fabricated using standard photolithography techniques on a 4" Silicon wafer to create a negative mold of herringbone structures (Stott, S. L., et al., PNAS 107: 18392-18398, 2010; Duffy, D. C., et. al., Anal. Chem. 70: 4974-4984, 1998). A 10:1 mass ratio of a base and a curing agent SYLGARD® 184 A/B (Dow Corning) was poured on the wafer mold and baked overnight in an oven at 80° C. The cured polydimethyl-siloxane (PDMS) replica was removed from the mold and holes were punched through the PDMS for fluid connections. The PDMS devices were irreversible bonded to glass slides using oxygen plasma at 50 mW, 5 ccm for 30 seconds (PX-250, March Plasma Systems).

A 4% (w/v) Gelatin solution from Bovine (bloom 225, type B, Sigma Aldrich) was functionalized with sulfo-NSH-Biotin (Thermo Scientific) at a mass ratio of 3.5/1. The pH of the solution was adjusted at 7.4 and the reaction proceeded for 2 hours under stirring conditions and RT. The mixture was dialyzed for 48 hours at a volume ratio of 1:1000. Finally, the solution was freeze-dried for 1 week and storage at 4° C. until use. Biotinylation efficiency of the gelatin was determined using a standard colorimetric biotin assay (Thermo Scientific).

The gelatin coating was constructed using a modified layer-by-layer technique (LBL). A 1% (w/v) gelatin-biotin solution was directly flushed on the plasma activated surface of a microfluidic chip and incubated for 15 minutes. The excess of gelatin-biotin was washed with phosphate-buffer saline (PBS). A solution of 100 µg/ml Neutravidin was flushed into the device and incubated for 15 minutes. The incremental deposition of Neutravidin was verified with fluorescence microscopy. These steps were repeated up to the formation of four layers. A solution of 70 nm streptavidin-coated nanoparticles (Spherotech) was added to the gelatin coating for the deposition of biotinylated antibodies: anti-EpCAM, anti-HER2, anti-EGFR; at 10 µg/ml each one.

The modified LBL process produced very uniform layers on complex 3-D microfluidic structures such as grooves or herringbones. The thickness of the gelatin coating was characterized using a Dektar 150 Surface Profiler (Veeco). A minimum of three different gels for each condition were quantification. Thickness measurements of the gelatin showed that there was approximately 33.75 nm increase per deposited layer (FIG. 1C) and four to six layers were deposited. The thickness of the physisorbed layer (E) depended on the initial concentration of gelatin-biotin. For a 0.1% (V/W) solution at 20° C., the thickness of the physisorbed layer was 5.4±2.34 nm; while for a 1% (V/W) solution, the thickness was 18.2±7.51 nm.

Figure 2A:
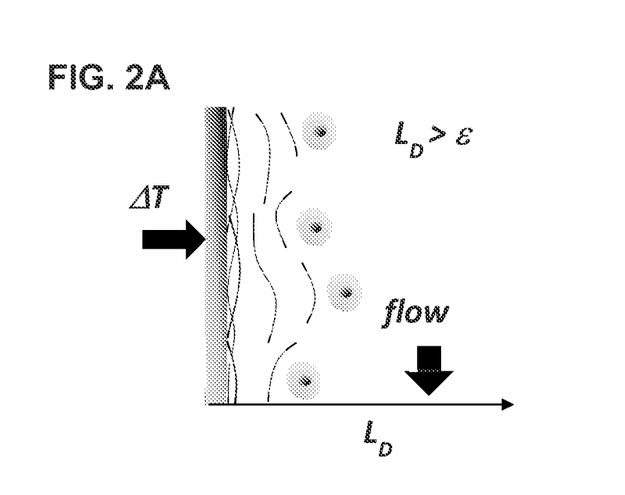
FIG. 2A is a schematic illustration of the mechanism of bulk release.
Figure 2B:
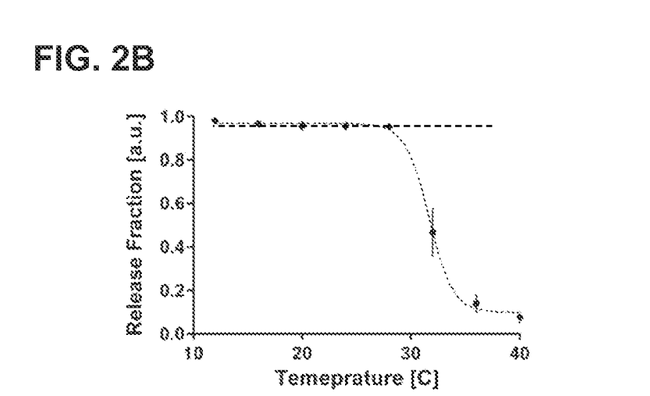
FIG. 2B is a dot plot showing the release fraction of particles immobilized on the surface of the capture system.

FIG. 2A illustrate the process of bulk release, in which the total thickness of the layers was thicker than the thickness of the initial physisorbed gelatin layer ($L_D$=135.0±11.2 nm>ε). For bulk release of captured CTCs, a heating stage with a temperature controller was used (Bioscience tools). The Temperature on the microfluidic device was increased from room temperature (RT) to 37° C. and maintained for 10 min without flow conditions. During this time, cells started to detach from the surface of the microfluidic chip and were collected at the outlet of the device applying a flow rate of 1.5 to 2.5 ml/h. As shown in FIG. 2B, the detachment of the gelatin layers was negligible with a retention fraction of 0.961±0.011, when the temperature is below 30° C. Statistical analysis between the first five time points revealed no significant difference (p<0.05). An increment in temperature over 30° C. produced the detachment of the external gelatin layers, and pressure driven flow removed the gelatin layer from the system, a residual fraction of 0.109±0.05 of the gelatin layer remained on the surface of the device (FIG. 2B). As expected, changes in the flow rate in the range of 2.0 to 3.5 mL/h did not produce significant variations in the amount of degradation of the gelatin layers.

Statistical comparisons of two groups were performed using the Student's t-test. For multiple group comparisons, one-way analysis of variance (ANOVA) was performed. A $p<0.05$ was considered statistical significant between compared groups.

Figure 3A:
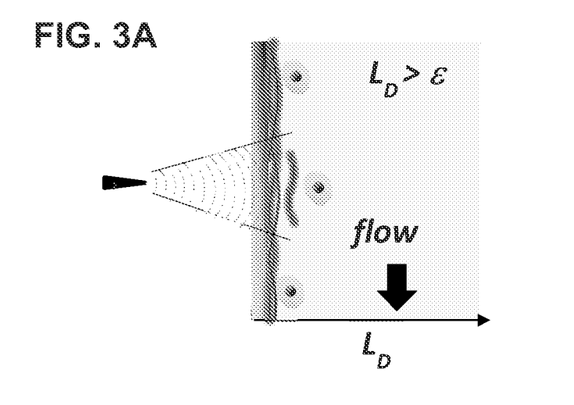
FIG. 3A is a schematic illustration of the mechanism of selective release.
Figure 3B:
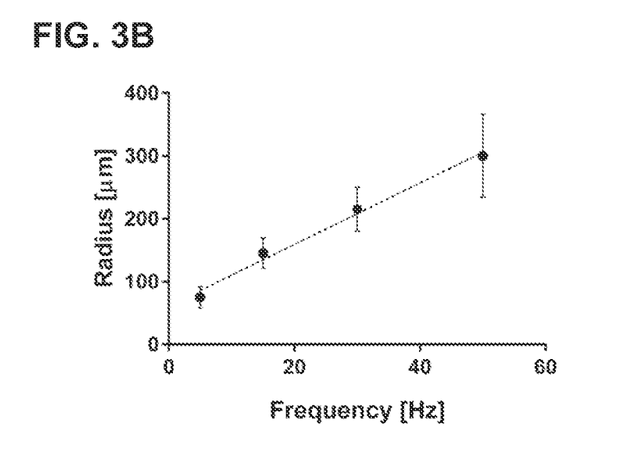
FIG. 3B is a dot plot showing sizes of the release radius based on the input frequency of vibration that creates a localized shear stress.

FIG. 3A illustrates the mechanism of selective release. For selective release of captured CTCs from the surface coating, an external controlled force was applied on the surface of the chip such that it created a localized shear stress on the surface of the gelatin film. The shear force at the surface of the film produced the detachment of the cell. Cells released within the release radius were collected at the outlet of the device applying a flow rate of 1.5 to 2.5 ml/h. An experimental device for releasing CTCs was built (see FIG. 4A). The microtip produced a controlled vibration at the surface of the chip such that the gelatin layer was locally removed by shear stress. The sizes of the gelatin layer removed depended on the frequency of vibration and a release radius was defined (FIG. 3B).

Nanoparticles were incorporated into the system for the immunoaffinity capture of target cells, e.g., CTCs. This capture-layer consisted of a uniform deposition of streptavidin coated nanoparticles (at 7.31 nmole of antibody per 1 mg of nanoparticle) on top of the gelatin film. The nanoparticles interacted with the surface by the strong ($K_d \sim 10^{-15}$ M) biotin-streptavidin binding. Fluorescently labeled Biotin-RPE was used to determine that the nanoparticles still had available binding sites for capture antibodies and they were not completely embedded on the gelatin film.

These results show that an example of a particle capture system as disclosed herein can be synthesized using standard techniques.

Example 2: A Device for Selectively Releasing Captured Particles in a Gel

Figure 4B:
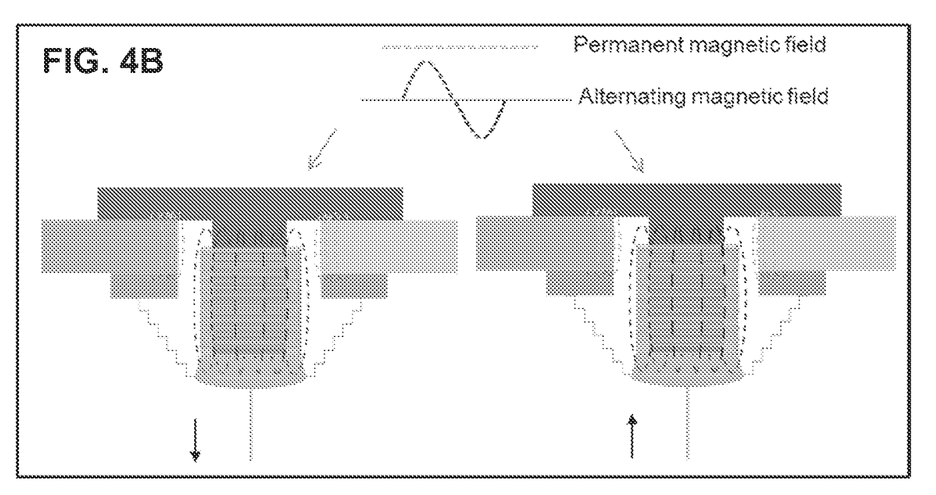
FIG. 4B is a schematic illustration of operation of the device shown in FIG. 4A.

A prototype device for selectively releasing captured particles was built by converting a stereo speaker system into a microtip transducer (FIG. 4A). A microtip of diameter 80 μm (Warner Instruments) was mounted directly on the center of a copper coil using superglue. The microtip transducer was controlled with the presence of two magnetic fields (FIG. 4B): one permanent magnetic field produced by the magnet; and an alternating magnetic field produced by the cupper coil. The alternating magnetic field was created using a function generator (BK Precision) with a fixed voltage peak to peak (VPP) of 20 V. The range of the input frequencies was 5 to 60 Hz. A sinusoidal input signal was used for all the release experiments. The displacement of the microtip transducer was controlled with the input frequency. The microtip transducer was mounted in a stage with only movement in the z-direction (to bring it into contact with the Gel-Chip). The Gel-Chip was mounted on a motorized microscope stage such that target cells were positioned within the release radius of the microtip.

These results show an example of a device that can be used for selectively releasing captured particles.

Example 3: Capture of Cancer Cell Lines

Prostate (PC3), Breast (SKBR3, MDA-MD-231), and lung (H1650) cancer cell lines were obtained from the American Type Culture Collection (ATCC) and expanded according standard cell culture protocols. At 85% cell confluence, cells were stained with cell tracker green (Invitrogen), and then trypsinized. Stained cells were spiked into blood at 1000 cells/ml of healthy donor blood and run through the microfluidic device. For CTC capture and non-specific cell binding quantification, an automatic imaging protocol was used. For quantification of release cells, the microfluidic chip was imaged before and after release and the difference of the counted cells was defined as the percentage of released cells.

Figure 5A:
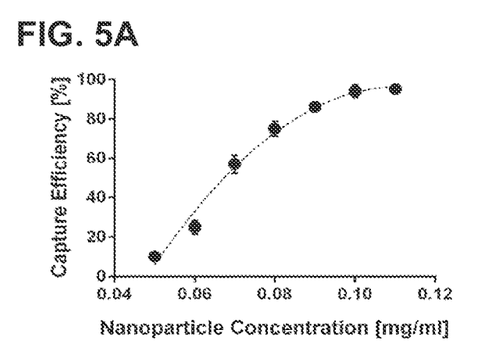
FIG. 5A is a dot plot showing that capture efficiency depends on the concentrations of nanostructures.
Figure 5B:
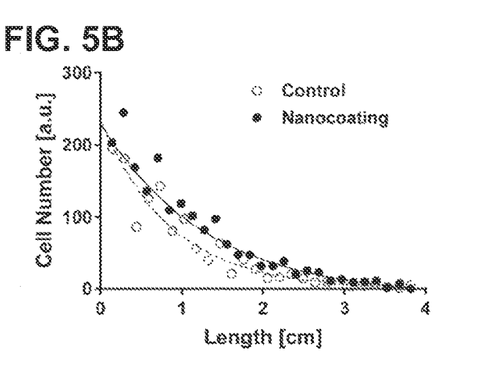
FIG. 5B is a dot plot showing the specificity of captured target cells.

The particle capture system was optimized for maximum isolation of CTCs from whole blood. Target PC3 prostate cancer cells were used (1000 cells spiked in 1 ml of blood). As indicated in FIG. 5A, for nanoparticle concentrations below 0.05 mg/ml, capture efficiency was 10%±2.34%. As expected, an increase in nanoparticle concentration also reflected as an increase in capture efficiency. It was determined that a nanoparticle concentration of 0.11 mg/ml was optimal; producing a capture efficiency of over 95%±1.45%. Further addition of nanoparticle concentration did not increase capture efficiency of the Gel-chip. Specificity of antibody capture on the Gel-Chip was compared with our previous functionalization chemistry protocols (Stott, S., et. al., Proceedings of the National Academy of Sciences 107, 18392-18397, 2010). Typically, it was observed a depletion pattern across the length of the devices. Heat maps of specific capture were fitted to a single exponential decay model as showed on FIG. 5B. However, the exponential coefficients for both conditions were different: 1.146 for the standard, and 0.764 for the film. Non-specific binding (NSB) of white blood cells (WBC) did not show a decay pattern across the length of the Gel-chip.

Figure 5C:
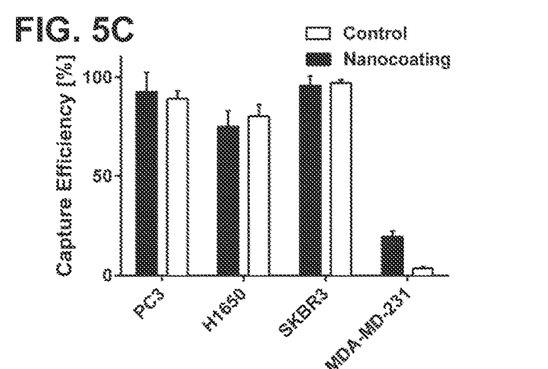
FIG. 5C is a bar graph comparing capture efficiency of one implementation of the present gelatin particle capture system with that of a control chip without the responsive gelatin coating for different cancer cell lines.
Figure 5D:
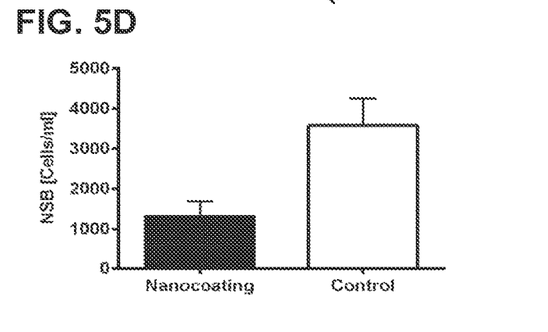
FIG. 5D is a bar graph showing non-specific cell binding on the present gelatin particle capture system or on a control.

The capture efficiency of different cancer cell lines on the Gel-Chip was compared with the capture efficiency of our previous $^{HB}$Chip using anti-EpCAM alone as a capture antibody. Cancer cell lines with different levels of EpCAM antigen expression were used: Prostate (PC3), lung (H1650), and breast (SKBR3, and MDA-MD-231) cells. For cancer cell lines with high EpCAM expression, comparisons of the mean values of capture efficiency did not show significant differences (p>0.05). In FIG. 5C, PC3, H1650, and SKBR3 cells were captured at efficiencies of 92.43%±9.69%, 75%±7.91%, and 95.67%±4.93% for the Gel-Chip; and 89%±4.00%, 80.33%±% 5.69, and 97.33%±1.73% for the $^{HB}$Chip. However, for a cancer cell line with low EpCAM expression (MDA-MD-231), there was a significant increase in capture efficiency in the Gel-Chip with 19.01%±2.86% and 3.43%±0.85% (p<0.05, n=4) for the Gel-Chip and the $^{HB}$Chip, respectively. The purity of captured cancer cells among contaminating leukocytes was 47.23%±0.34% for the Gel-Chip, compared to 14.0%±0.1% for the $^{HB}$Chip. Additionally, the Gel-Chip offered the advantage of low NSB compared to the $^{HB}$Chip (FIG. 5D). The overall value for NSB per ml of blood in the Gel-Chip was 1307±376.83 cells, while in the HB-Chip was 3507±676.16 cells for two different flow rates tested (1.2 and 1.5 ml/h, p<0.05).

These results show that a particle capture system as disclosed herein can be used to selectively capture cancer cells.

Example 4: Release of Cancer Cell Lines

Figure 6A:
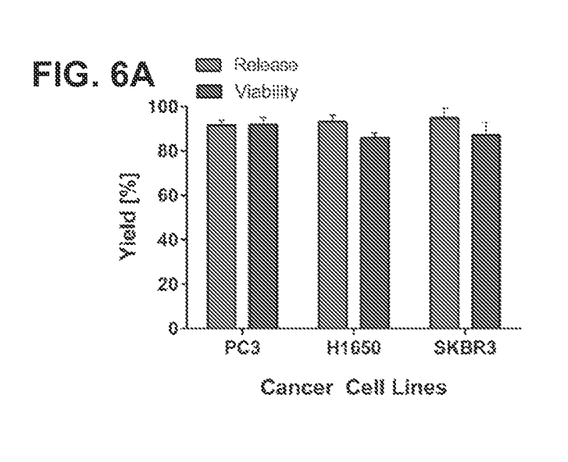
FIG. 6A is a bar graph comparing the release efficiency and viability of different cancer cell lines by bulk release by increasing temperature.

The Gel-Chip allowed the recovery of capture cells from its surface with two different mechanisms. For bulk release (FIG. 6A), the process had an efficiency of 91.49%±2.32%, 93.83%±2.89%, and 97%±4.45 for PC3, H1650, and SKBR3 cells respectively (p>0.05). Therefore, release efficiency was considered independent of cancer cell phenotype or levels of EpCAM expression (data not shown). The biocompatibility of the release mechanism was evaluated in FIG. 6A, which shows no significant differences for viability (p>0.05): 93.03%±3.17% (PC3), 85.94%±2.30% (H1650), and 87.25%±5.51% (SKBR3). Released cells were immobilized in glass slides for fixation and stained for CTC and WBC markers. Additionally, released cells were cultured on a 96-well plate for up to 7 days and it was observed that cells were able to form colonies and get confluent (data not shown).

Figure 6B:
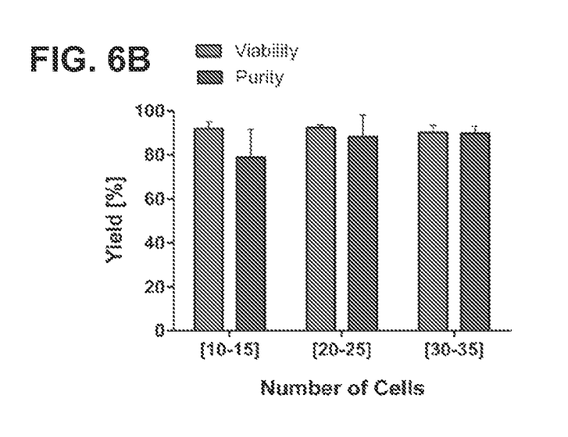
FIG. 6B is a bar graph showing viability and purity of selectively released PC3 cells from the particle capture system.

For selective release, PC3 cancer cells were individually released and grouped in three categories (FIG. 6B, data not shown). The viability of the recovered cells for the different cell groups were over 91.67±1.42% with no significant difference between groups (p>0.05), which was consisted with viability values obtained for bulk release (FIG. 6B). Recovered cells were able to grow overtime and form colonies. In addition, selective release achieved remarkable values of purity, with values up to 89.74%±3.25% (FIG. 6B when cells where released sequentially and many individual events of 100% purity.

These results show that a particle capture system as disclosed herein can release the captured cancer cells by either bulk release or selective release.

Example 5: Analysis of CTCs from Clinical Samples

Blood from patients with advance lung, breast, prostate cancer and healthy donors was collected according to a protocol approved by the institutional review board (JRB). A total of 13 patients (6 breast, 4 lung, and 3 prostate), who received treatment at the Massachusetts General Hospital Cancer Center donated 10-20 ml of blood during multiple times for analysis on the microfluidic device. All specimens were collected into vacutainer (Becton-Dickinson) tubes containing the anticoagulant EDTA and were processed within 4 h of blood draw. A 5 ml aliquot of patient or healthy donor blood was run in custom built microfluidic processing machine using methods described before (Nagrath, S., et al. Nature 450: 1235-1239, 2007; Stott, S. L. et al., Science Translational Medicine 2: 1-10, 2010).

To maximize capture of CTCs on the Gel-Chip, an antibody cocktail of biotinylated anti-EpCAM, anti-HER2, and anti-EGFR was used. An average of 3.5 ml of blood from 16 metastatic cancer patients at different stages of treatment were processed through the Gel-Chip (n=8 for breast cancer, and n=8 for lung cancer). CTCs were capture in 14 of 16 patient samples (87.5%). Some samples were analyzed on the Gel-Chip.

For inmmunofluorescence staining, anti-EPCAM, anti-EGFR, anti-MET, anti-SOX2, and anti-WSCK were used as tumor markers, and anti-CD45 as leukocyte marker. Nuclear DNA content was stained with 4,6-diamidino-2-phenylindole or DAPI. Specifically, captured cells on the HB chip were fixed with 4% paraformaldehyde and washed with PBS immediately following blood processing. The fixed cells were permeabilized with 1% NP40 and blocked with 2% normal goat serum/3% BSA before the addition of primary antibodies for immunostaining. The primary antibodies used for CTC targeting were rabbit wide spectrum anti-cytokeratin (1:100, ABCAM), rabbit anti-MET (1:1000, BD Biosciences), anti-SOX2 (1:50, BD Biosciences) and anti-EGFR (1:200, BD Biosciences). Anti-CD45 mlgG1 (1:100, BD Biosciences) was added to target white blood cells. Next, secondary immunofluorescent labeled antibodies were added to amplify the signal along with DAPI to label the nuclei. The secondary antibodies used were goat anti-rabbit Alexa Flour 488 (1:200, Jackson) and goat anti-mouse IgG1 Alexa Flour 594 (1:200, Jackson). Following staining, the devices were washed with PBS and stored at 4° C.

For live immune-fluorescent staining, CTCs were identified with mouse anti-EpCAM (3:100, Cell Signaling), anti-Cadherin11 (1:10, R&D Systems), and anti-Axl (1:10, R&D Systems) conjugated to Alexa Flour 488. White blood cells were targeted with mouse anti-CD45 (1:20, BD Biosciences), anti-CD16 (1:20, BD Biosciences), and anti-CD-14 (1:20, BD Biosciences) conjugated to PE-CF 594.

CTCs for electron microscopy were fixed with 2% glutaraldehyde in a 0.2 M sodium cacodylate for 2 hours. Fixed samples were dehydrated in steps in ethanol dilutions. Ethanol was removed using a critical point dryer (Auto Samdri 815 A, Tousimis), and sputtered with gold/palladium for 60 sec at 20 mA (208HR Cressington). Imaging was performed using a field emission scanning electron microscope (SUPRA 55 VP, Zeiss).

Figure 7A:
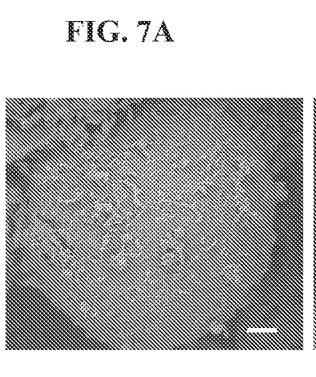
FIGS. 7A to 7C are a set of electron microscopy images of CTCs from a breast cancer patient captured on the present capture system.
Figure 7B:
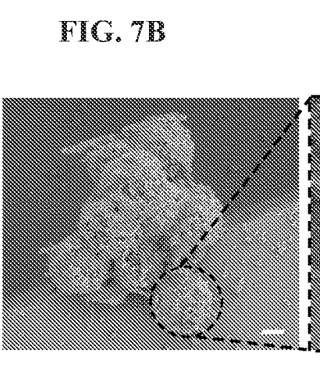
Figure 7C:
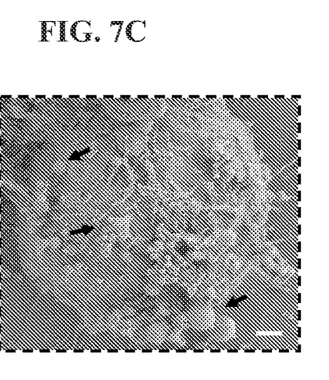

Although the antibody cocktail was very specific and allowed clear threshold values for CTCs and leukocytes, a very small number of "double positive" events were detected; these cells were excluded from any analysis. The Gel-Chip allowed the capture of clusters of CTCs from different cancer patients. Cluster of CTCs varied in size, shape, and number of cells. The minimum number of CTCs to be considered as a cluster was four tumor cells. Comparisons of the surface morphology of different CTCs revealed they were very heterogeneous with some CTCs having micrometer-size vesicles attached to them (FIGS. 7A-C).

The number of captured CTCs for breast cancer patients varied from 0 to 45.43 CTCs/mL, whereas the number was 0 to 6.56 CTCs/mL for lung cancer patients. Clusters of CTCs were identified in 37.5% and 25% of breast and lung cancer patients, respectively. Captured CTCs were released from the Gel-Chip using bulk or selective degradation of the film. Released CTCs were immobilized in PLL coated glass slides and stained for immunofluorescence. The shape, morphology of CTCs as well as their interactions with leukocytes or other CTCs has been maintained during the release process (data not shown). For patients who showed CTC aggregates or clusters, the number of clusters was quantified (single, double, triple or cluster of CTCs). As expected single CTCs are more common along with breast and lung patients when compared to CTC clusters numbers (data not shown). The size distribution of the different CTCs present for breast and lung cancer patients was analyzed such that an average of 11.35±1.23 µm and 13.45±1.25 µm for breast and lung CTCs respectively, whereas WBC exhibited an average of 10.06±2.34. Although the values obtained did not show statistical difference (p>0.05).

For genotyping analysis, three breast and one lung cancer patients with metastatic disease that were previously characterized to contain hotspot mutations in the PIK3CA and EGFR oncogenes, respectively, were selected. Hematoxylin and eosin (H&E) stain of the primary tumors is performed for each of the four patients (data not shown). At the time of diagnosis, fine needle aspirates (FNAs) from the primary tumor site were used to determine the mutational profile of each of the four patients. Particularly, Br3, Br4, and Br5 tumors resulted positive for the 3140A/G (H1047R) heterozygous mutation in the PIK3CA gene, while Lu1 tumor was positive for the exon 19 deletion in the EGFR gene. Single CTCs isolated from the blood of the same breast and lung cancer patients were used for comparison. First, CTCs were captured on the Gel-Chip and then stained with Alexa488-conjugated antibodies against EpCAM, and anti- Cadherin11. PE-CF 594-conjugated antibodies against CD14, CD16 and CD45 were used to exclude contaminating leukocytes. Selective release was used to recover Alexa488-positive single CTCs without additional steps.

Genomic DNA was then extracted from the released CTCs with AllPrep® DNA/RNA micro kit (Qiagen) according to the manufacturer's instructions, and subjected to targeted PCR to amplify the region of interest. For the PIK3CA Exon 9 and Exon 20 mutational studies as well as the EGFR exon 19 deletion, two PCR rounds of 35 cycles each were performed with previously described primers (Barbi, S. et al. J Exp Clin Cancer Res. 29: 32, 2010; Mitsudomi, T. & Yatabe, Y., FEBS Journal 277: 301-308, 2010) or primers were designed to be specific for the known mutations to be detected.

Bands were visualized by standard gel electrophoresis. Amplicons were purified by an Agencourt AMPure XP bead (Beckman Coulter) cleanup step prior to sequencing at the MGH DNA Core Facility. Additionally, all appropriate controls were run with cell lines and white blood cells. The amplified bands of interest were observed for the different mutations (data not shown).

Sequencing was performed with a fluorescently-labeled dideoxy-nucleotide chain termination method. Ultimately, the 3140A/G (H1047R) mutation was found in the PIK3CA gene in all three breast CTC samples, as well as the exon 19 deletion in the EGFR gene in the lung CTC sample which constituted direct evidence that the Gel-Chip can be used as a platform for selective release and single cell genetic interrogation of CTCs obtained from the blood of patients with cancer.

These results show that the particle capture systems can selectively capture and release target particles as disclosed herein and thus have useful clinical applications.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A system for selectively capturing and releasing one or more target particles from a liquid sample, the system comprising:
a substrate;
a first layer of gelatin bound to the substrate by physical adsorption without gelling, wherein the gelatin is functionalized with a plurality of first members of a binding pair;
a second layer of temperature-responsive gelatin wherein the second layer of temperature sensitive gelatin is functionalized with a plurality of the first members of the binding pair, wherein the first layer of gelatin melts at a higher temperature than the second layer of gelatin, and wherein the second layer is bound to the first layer via a plurality of second members of the binding pair that are associated with the first members of the binding pair on both the first and the second layers;
optionally, one or more subsequent layers of gelatin, each bound to a previous layer by the second members of the binding pair; and
a plurality of nanostructures, wherein the nanostructures are bound to the second members of the binding pair and to one or more particle-binding moieties labeled with the second member of the binding pair, wherein the one or more particle-binding moieties selectively bind to the target particles, wherein the nanostructures are bound to a top layer of gelatin by the second members of the binding pair.

2. A method of selectively capturing and releasing one or more target particles from a liquid sample, the method comprising:
obtaining a system of claim 1;
contacting the sample to the system to enable the one or more particle-binding moieties to bind to target particles in the sample releasing the bound target particles from the system of claim 1 by melting the second or subsequent gelatin layers at a temperature that does not melt the first layer of gelatin.

3. The method of claim 2, wherein the melting temperature of the second or subsequent gelatin layers is 37° C.

4. The system of claim 1, wherein the target particles are living cells or microvesicles.

5. The system of claim 4, wherein the living cells are circulating tumor cells.

6. The system claim 1, wherein the one or more particle-binding moieties comprise antibodies.

7. The method of claim 6, wherein the antibodies comprise one or more of anti-EpCAM, anti-HER2, and anti-EGFR antibodies.

8. The system claim 1, wherein the substrate comprises a flat slide, a channel in a microfluidic device, or a microbead.

9. A method of making a target particle capturing system, the method comprising:
(a) obtaining a substrate;
(b) forming a first layer of gelatin on the substrate by physical adsorption without gelling, wherein the gelatin is functionalized with a plurality of first members of a binding pair;
(c) contacting the first layer of gelatin with second members of the binding pair;
(d) forming a second layer of temperature-responsive gelatin wherein the gelatin is functionalized with a plurality of the first members of the binding pair wherein the first layer of gelatin melts at a higher temperature than the second layer of gelatin, and the second layer is bound to the first layer via a plurality of second members of the binding pair that are associated with the first members of the binding pair on both the first and the second layers;
(d) optionally forming one or more subsequent layers of gelatin, each bound to a previous layer by second members of the binding pair; and
(e) contacting the last formed gelatin layer with a solution comprising nanostructures, wherein the nanostructures are bound to second members of the binding pair and to one or more particle-binding moieties labeled with the second member of the binding pair, wherein the one or more particle-binding moieties selectively bind to the target particles.

10. The method of claim 9, wherein the target particles are living cells or microvesicles.

11. The method of claim 10, wherein the living cells are circulating tumor cells.

12. The method of claim 9, wherein the one or more particle-binding moieties comprise antibodies.

13. The method of claim 12, wherein the antibodies comprise one or more of anti-EpCAM, anti-HER2, and anti-EGFR antibodies.

* * * * *

UNITED STATES PATENT AND TRADEMARK OFFICE
CERTIFICATE OF CORRECTION

PATENT NO. : 10,551,376 B2
APPLICATION NO. : 14/764855
DATED : February 4, 2020
INVENTOR(S) : Eduardo Reategui, Shannon Stott and Mehmet Toner Page 1 of 1

It is certified that error appears in the above-identified patent and that said Letters Patent is hereby corrected as shown below:

In the Claims

In Column 16, Line 23 (approx.), Claim 6, after "system" insert -- of --

In Column 16, Line 24 (approx.), Claim 7, delete "method" and insert -- system --

In Column 16, Line 28 (approx.), Claim 8, after "system" insert -- of --

In Column 16, Line 47 (approx.), Claim 9, delete "(d)" and insert -- (e) --

In Column 16, Line 50 (approx.), Claim 9, delete "(e)" and insert -- (f) --

Signed and Sealed this
Twentieth Day of October, 2020

Andrei Iancu
*Director of the United States Patent and Trademark Office*